United States Patent
Barner et al.

(10) Patent No.: US 9,517,334 B2
(45) Date of Patent: Dec. 13, 2016

(54) LEAD ANCHORS AND SYSTEMS AND METHODS EMPLOYING THE LEAD ANCHORS

(71) Applicant: BOSTON SCIENTIFIC NEUROMODULATION CORPORATION, Valencia, CA (US)

(72) Inventors: Paul Keith Barner, Valencia, CA (US); Joshua Dale Howard, Chatsworth, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/457,602

(22) Filed: Aug. 12, 2014

(65) Prior Publication Data

US 2015/0051674 A1   Feb. 19, 2015

Related U.S. Application Data

(60) Provisional application No. 61/867,394, filed on Aug. 19, 2013.

(51) Int. Cl.
*A61N 1/05* (2006.01)

(52) U.S. Cl.
CPC ..... *A61N 1/0558* (2013.01); *A61N 2001/0582* (2013.01)

(58) Field of Classification Search
None
See application file for complete search history.

(56) References Cited

U.S. PATENT DOCUMENTS

| 3,866,615 A | 2/1975 | Hewson |
| 4,141,752 A | 2/1979 | Shipko |
| 4,276,882 A | 7/1981 | Dickhudt et al. |

(Continued)

FOREIGN PATENT DOCUMENTS

| EP | 85417 A1 | 8/1983 |
| EP | 0597213 A1 | 5/1994 |

(Continued)

OTHER PUBLICATIONS

U.S. Appl. No. 14/457,640, filed Aug. 12, 2014.
U.S. Appl. No. 14/452,467, filed Aug. 5, 2014.
U.S. Appl. No. 14/312,194, filed Jun. 23, 2014.

*Primary Examiner* — Erica Lee
(74) *Attorney, Agent, or Firm* — Lowe Graham Jones PLLC; Bruce E. Black

(57) ABSTRACT

A lead anchor including a body having a first end and a second end opposite to the first end is disclosed. The body defines a lead lumen extending from the first to the second end and can receive a lead. The lead anchor also includes a fastening mechanism disposed in the body and in communication with the lead lumen. The fastening mechanism can fasten the received lead to the lead anchor when actuated by a user. The lead anchor also includes tabs(s) extending from the body and tags. Each tag includes an anchor attachment element and a cylindrical implantation element coupled to the anchor attachment element. The anchor attachment element is affixed to one of the tabs. The cylindrical implantation element anchors the lead anchor into patient tissue by insertion of the implantation element into the patient tissue using a needle insertion tool.

19 Claims, 9 Drawing Sheets

(56) References Cited

U.S. PATENT DOCUMENTS

| | | |
|---|---|---|
| 4,316,471 A | 2/1982 | Shipko et al. |
| 4,462,401 A | 7/1984 | Burgio |
| 4,632,670 A | 12/1986 | Mueller, Jr. |
| 4,764,132 A | 8/1988 | Stutz, Jr. |
| 4,858,623 A | 8/1989 | Bradshaw et al. |
| 5,036,862 A | 8/1991 | Pohndorf |
| 5,107,856 A | 4/1992 | Kristiansen et al. |
| 5,158,097 A | 10/1992 | Christlieb |
| 5,228,248 A | 7/1993 | Haddock |
| 5,269,809 A | 12/1993 | Hayhurst et al. |
| 5,370,662 A | 12/1994 | Stone et al. |
| 5,376,108 A | 12/1994 | Collins et al. |
| 5,484,445 A | 1/1996 | Knuth |
| 5,865,843 A | 2/1999 | Baudino |
| 5,895,360 A | 4/1999 | Christopherson et al. |
| 5,957,968 A | 9/1999 | Belden et al. |
| 6,181,969 B1 | 1/2001 | Gord |
| 6,192,279 B1 | 2/2001 | Barreras, Sr. et al. |
| 6,360,750 B1 | 3/2002 | Gerber et al. |
| 6,473,654 B1 | 10/2002 | Chinn |
| 6,516,227 B1 | 2/2003 | Meadows et al. |
| 6,606,523 B1 | 8/2003 | Jenkins |
| 6,609,029 B1 | 8/2003 | Mann et al. |
| 6,609,032 B1 | 8/2003 | Woods et al. |
| 6,741,892 B1 | 5/2004 | Meadows et al. |
| 6,792,314 B2 | 9/2004 | Byers et al. |
| 6,847,849 B2 | 1/2005 | Mamo et al. |
| 6,901,287 B2 | 5/2005 | Davis et al. |
| 6,978,180 B2 | 12/2005 | Tadlock |
| 6,984,145 B1 | 1/2006 | Lim |
| 7,069,083 B2 | 6/2006 | Finch et al. |
| 7,072,719 B2 | 7/2006 | Vinup et al. |
| 7,161,461 B1 | 1/2007 | Nelson |
| 7,244,150 B1 | 7/2007 | Brase et al. |
| 7,343,202 B2 | 3/2008 | Mrva et al. |
| 7,437,193 B2 | 10/2008 | Parramon et al. |
| 7,447,546 B2 | 11/2008 | Kim et al. |
| 7,610,102 B2 | 10/2009 | Kowalczyk |
| 7,672,734 B2 | 3/2010 | Anderson et al. |
| 7,761,165 B1 | 7/2010 | He et al. |
| 7,787,960 B2 | 8/2010 | Lubenow |
| 7,848,803 B1 | 12/2010 | Jaax et al. |
| 7,853,321 B2 | 12/2010 | Jaax et al. |
| 7,949,395 B2 | 5/2011 | Kuzma |
| 7,974,706 B2 | 7/2011 | Moffitt et al. |
| 8,175,710 B2 | 5/2012 | He |
| 8,224,450 B2 | 7/2012 | Brase |
| 8,224,451 B2 | 7/2012 | Jaax et al. |
| 8,229,573 B2 | 7/2012 | Chen et al. |
| 8,315,704 B2 | 11/2012 | Jaax et al. |
| 8,364,278 B2 | 1/2013 | Pianca et al. |
| 2001/0000187 A1 | 4/2001 | Peckham et al. |
| 2002/0107554 A1 | 8/2002 | Biggs et al. |
| 2003/0074023 A1 | 4/2003 | Kaplan et al. |
| 2003/0078623 A1 | 4/2003 | Weinberg et al. |
| 2003/0208247 A1 | 11/2003 | Spinelli et al. |
| 2004/0059392 A1 | 3/2004 | Parramon et al. |
| 2005/0033393 A1 | 2/2005 | Daglow |
| 2005/0165465 A1 | 7/2005 | Pianca et al. |
| 2005/0283202 A1 | 12/2005 | Gellman |
| 2005/0288760 A1 | 12/2005 | Machado et al. |
| 2006/0127158 A1 | 6/2006 | Olson et al. |
| 2006/0161235 A1 | 7/2006 | King |
| 2006/0173520 A1 | 8/2006 | Olson |
| 2006/0205995 A1 | 9/2006 | Browning |
| 2006/0206162 A1 | 9/2006 | Wahlstrand et al. |
| 2006/0235484 A1 | 10/2006 | Jaax et al. |
| 2007/0010794 A1 | 1/2007 | Dann et al. |
| 2007/0050005 A1 | 3/2007 | Lauro |
| 2007/0078399 A1 | 4/2007 | Olson |
| 2007/0100348 A1 | 5/2007 | Cauthen et al. |
| 2007/0150036 A1 | 6/2007 | Anderson |
| 2007/0219595 A1 | 9/2007 | He |
| 2007/0255369 A1 | 11/2007 | Bonde et al. |
| 2008/0071320 A1 | 3/2008 | Brase |
| 2008/0091255 A1 | 4/2008 | Caparso et al. |
| 2008/0140169 A1 | 6/2008 | Imran |
| 2008/0172116 A1 | 7/2008 | Mrva et al. |
| 2008/0183241 A1 | 7/2008 | Bedenbaugh |
| 2008/0183253 A1 | 7/2008 | Bly |
| 2008/0228251 A1 | 9/2008 | Hill |
| 2008/0243220 A1 | 10/2008 | Barker |
| 2008/0275401 A1 | 11/2008 | Sage et al. |
| 2008/0312712 A1 | 12/2008 | Penner |
| 2009/0018601 A1 | 1/2009 | Deininger et al. |
| 2009/0112272 A1 | 4/2009 | Schleicher et al. |
| 2009/0198312 A1 | 8/2009 | Barker |
| 2009/0210043 A1 | 8/2009 | Reddy |
| 2009/0254151 A1 | 10/2009 | Anderson et al. |
| 2009/0259260 A1 | 10/2009 | Bentley et al. |
| 2009/0270940 A1 | 10/2009 | Deininger |
| 2010/0094425 A1* | 4/2010 | Bentley et al. ............ 623/17.16 |
| 2010/0174240 A1 | 7/2010 | Wells et al. |
| 2010/0274336 A1 | 10/2010 | Nguyen-Stella et al. |
| 2010/0312319 A1 | 12/2010 | Barker |
| 2011/0022142 A1 | 1/2011 | Barker et al. |
| 2011/0060395 A1 | 3/2011 | Cantlon |
| 2011/0178573 A1 | 7/2011 | Nguyen-Stella et al. |
| 2011/0264180 A1 | 10/2011 | Hamilton |
| 2012/0150202 A1* | 6/2012 | Chen .................. A61B 17/0401 606/148 |
| 2012/0185027 A1 | 7/2012 | Pianca et al. |
| 2012/0232626 A1 | 9/2012 | Daglow |
| 2012/0277670 A1 | 11/2012 | Goetz |
| 2012/0283835 A1* | 11/2012 | Bentley ................ A61N 1/0558 623/17.16 |
| 2012/0330355 A1* | 12/2012 | Finley et al. .................. 606/232 |
| 2013/0204336 A1 | 8/2013 | Sharma |
| 2013/0238023 A1* | 9/2013 | Wales et al. .................. 606/232 |

FOREIGN PATENT DOCUMENTS

| | | |
|---|---|---|
| WO | 9833551 A1 | 8/1998 |
| WO | 99/53994 | 10/1999 |
| WO | 00/13743 A2 | 3/2000 |
| WO | 00/64535 | 11/2000 |
| WO | 2004/054655 | 7/2004 |
| WO | 2006/086363 A2 | 8/2006 |
| WO | 2007/056384 A2 | 5/2007 |
| WO | 2007/083108 A2 | 7/2007 |
| WO | 2007/149994 A2 | 12/2007 |
| WO | 2008/094789 A1 | 8/2008 |
| WO | 2008101026 A1 | 8/2008 |
| WO | 2008/121708 A2 | 10/2008 |
| WO | 2010/126853 A1 | 11/2010 |
| WO | 2012/151356 A1 | 11/2012 |
| WO | 2013112920 A1 | 8/2013 |

* cited by examiner

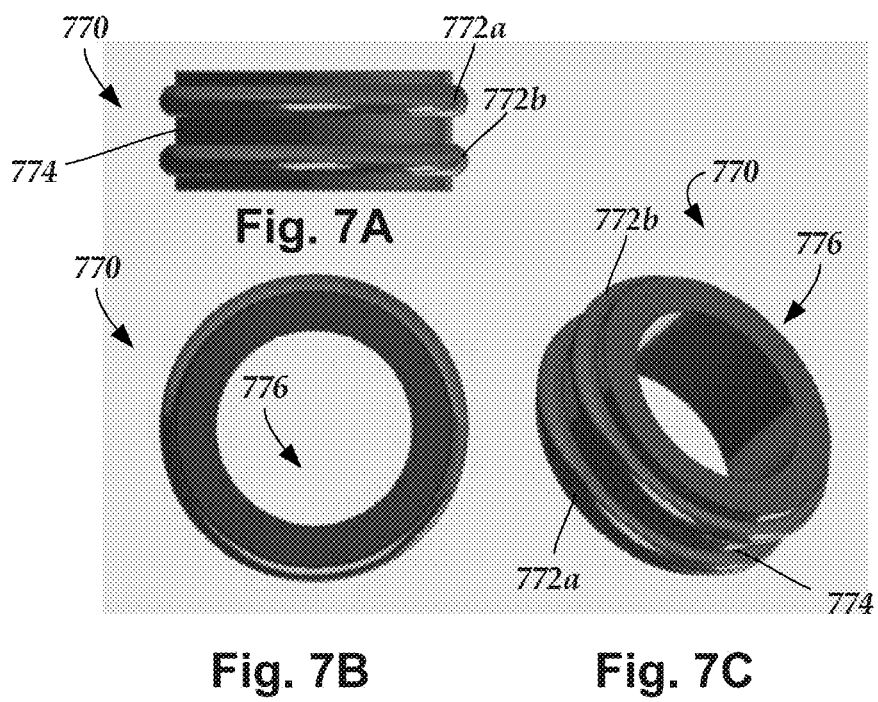

ND SYSTEMS AND
LEAD ANCHORS AND SYSTEMS AND METHODS EMPLOYING THE LEAD ANCHORS

CROSS-REFERENCE TO RELATED APPLICATIONS

This application claims the benefit under 35 U.S.C. §119(e) of U.S. Provisional Patent Application Ser. No. 61/867,394, filed Aug. 19, 2013, which is incorporated herein by reference.

FIELD

The present invention is directed to the area of implantable electrical stimulation systems and methods of making and using the systems. The present invention is also directed to lead anchors having anchoring tags as well as methods of making and using the lead anchors and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is a lead anchor including a body having a first end and a second end opposite to the first end. The body defines a lead lumen extending from the first end to the second end and can receive a lead. The lead anchor also includes a fastening mechanism disposed in the body which remains in communication with the lead lumen and is actuable by a user. The fastening mechanism can fasten the received lead to the lead anchor when actuated by the user. The lead anchor also includes a number of tabs extending from the body and a number of tags. Each tag includes an anchor attachment element and a cylindrical implantation element coupled to the anchor attachment element. The anchor attachment element is affixed to one of the tabs of the lead anchor. The cylindrical implantation element anchors the lead anchor into patient tissue by insertion of the implantation element into the patient tissue using a needle insertion tool.

Another embodiment is a method of anchoring a lead. The method includes inserting a portion of an electrical stimulation lead into the lead anchor described above. The method also includes fastening the lead anchor to the portion of the lead using the fastening mechanism of the lead anchor. The method also includes loading one or more of the cylindrical implantation elements into a needle insertion tool. The method further includes delivering the one or more of the cylindrical implantation elements into patient tissue using the needle insertion tool. Furthermore, the method includes releasing the one or more of the cylindrical implantation elements within the patient tissue to anchor the lead anchor and lead to the patient tissue.

Another embodiment is a kit including the lead anchor described above. The kit also includes an implantable electrical stimulation lead coupleable to the lead anchor.

A further embodiment is a lead anchor including a first body having a top surface, a first end, and a second end opposite to the first end. The top surface of the first body is non-flat with at least one peak or trough and can receive a portion of a lead disposed on the top surface from the first end to the second end. The lead anchor also includes a second body having a bottom surface, a first end, and a second end opposite the first end. The bottom surface conforms to the top surface of the first body so that the first and second bodies can be bound together to hold the lead between the first and second bodies.

Another embodiment is a kit including the lead anchor described above and an implantable electrical stimulation lead coupleable to the lead anchor.

Yet another embodiment is a kit including an implantable electrical stimulation lead including at least one lead body having a distal end portion, a proximal end portion, and a longitudinal length. The lead also includes a number of electrodes disposed along the distal end portion of the at least one lead body and a number of terminals disposed along the proximal end portion of the lead body. The lead also includes a number of conductors electrically coupling the terminals to the electrodes. The kit also includes an elastic suturing configured and arranged to dispose on, and compressively engage, a portion of the lead. The suture ring includes two circumferential ridges separated by a suture groove.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 7A is schematic side view of one embodiment of an elastic suture ring, according to the invention;

FIG. 7B is a schematic top view of the elastic suture ring of FIG. 7A, according to the invention;

FIG. 7C is a schematic perspective view of the elastic suture ring of FIG. 7A, according to the invention.

DETAILED DESCRIPTION

The present invention is directed to the area of implantable electrical stimulation systems and methods of making and using the systems. The present invention is also directed to lead anchors having anchoring tags, as well as methods of making and using the lead anchors and electrical stimulation systems.

Suitable implantable electrical stimulation systems include, but are not limited to, at least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated by reference.

Figure 1:
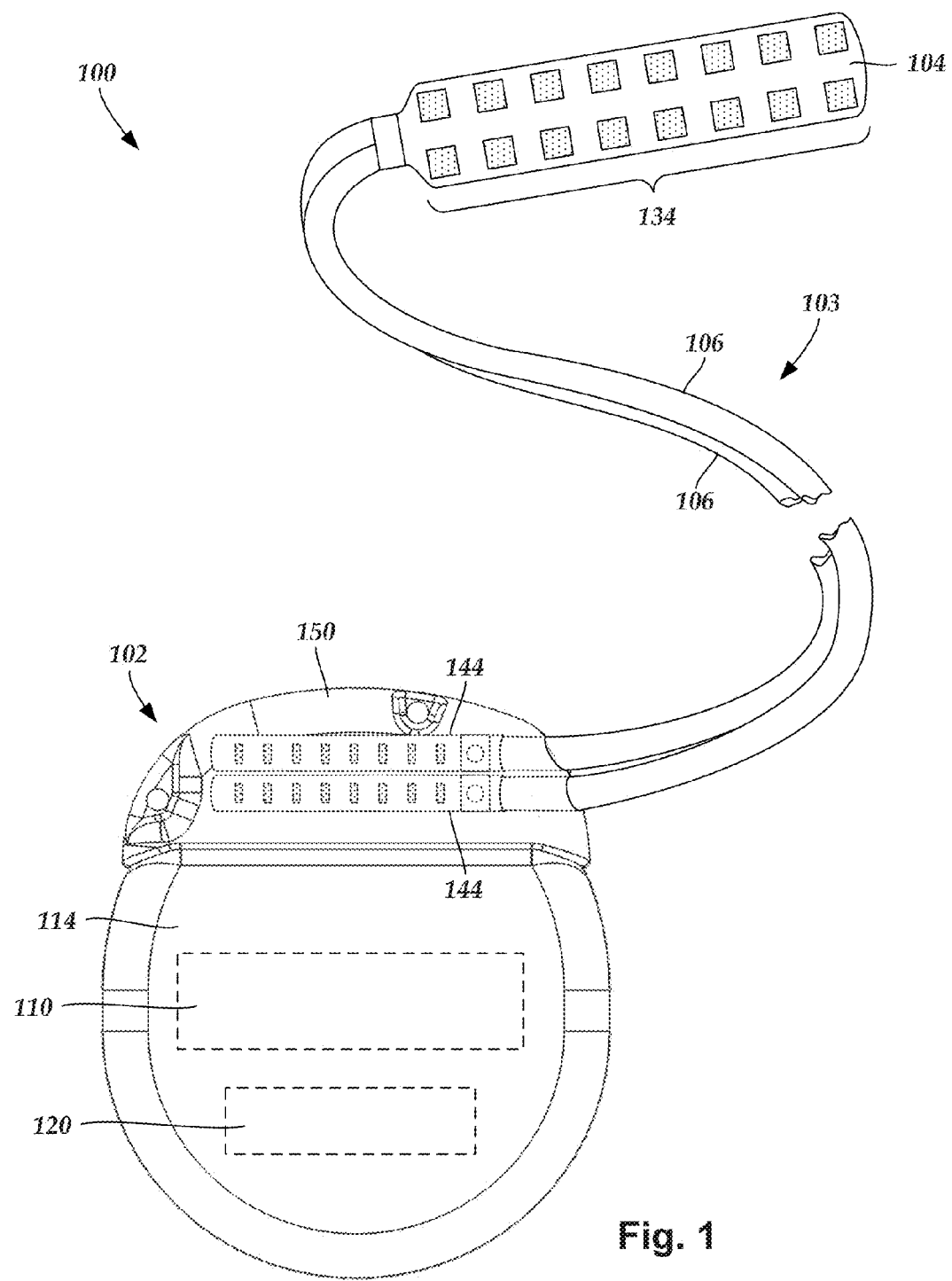
FIG. 1 is a schematic view of one embodiment of an electrical stimulation system that includes a paddle lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array of electrodes 133, such as electrode 134, is disposed on the paddle body 104, and an array of terminals (e.g., 210 in FIGS. 2A-2B) is disposed along each of the one or more lead bodies 106.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 2:
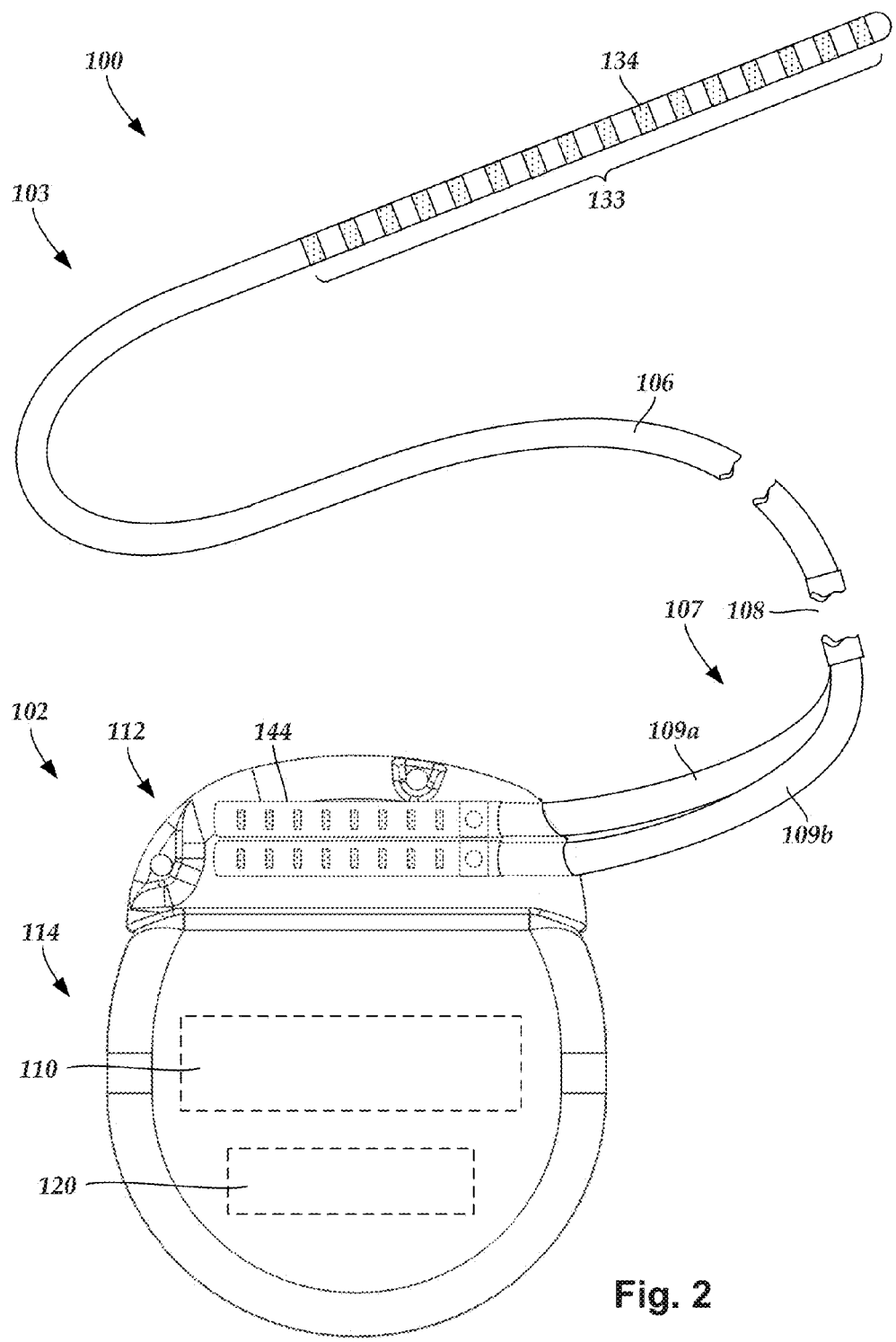
FIG. 2 is a schematic view of one embodiment of an electrical stimulation system that includes a percutaneous lead electrically coupled to a control module, according to the invention.

FIG. 2 illustrates schematically another embodiment of the electrical stimulation system 100, where the lead 103 is a percutaneous lead. In FIG. 2, the electrodes 134 are shown disposed along the one or more lead bodies 106. In at least some embodiments, the lead 103 is isodiametric along a longitudinal length of the lead body 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices (300 in FIGS. 3A-3B). For example, in at least some embodiments one or more lead extensions 324 (see e.g., FIG. 3B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 2, the electrical stimulation system 100 is shown having a splitter 207 configured and arranged for facilitating coupling of the lead 103 to the control module 102. The splitter 207 includes a splitter connector 208 configured to couple to a proximal end of the lead 103, and one or more splitter tails 209a and 209b configured and arranged to couple to the control module 102 (or another splitter, a lead extension, an adaptor, or the like).

The control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the lead including, for example, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes of the paddle body 104 (or one or more lead bodies 106) are typically disposed in, or separated by, a non-conductive, biocompatible material such as, for example, silicone, polyurethane, polyetheretherketone ("PEEK"), epoxy, and the like or combinations thereof. The one or more lead bodies 106 and, if applicable, the paddle body 104 may be formed in the desired shape by any process including, for example, molding (including injection molding), casting, and the like. The non-conductive material typically extends from the distal ends of the one or more lead bodies 106 to the proximal end of each of the one or more lead bodies 106.

In the case of paddle leads, the non-conductive material typically extends from the paddle body 104 to the proximal end of each of the one or more lead bodies 106. Additionally, the non-conductive, biocompatible material of the paddle body 104 and the one or more lead bodies 106 may be the same or different. Moreover, the paddle body 104 and the one or more lead bodies 106 may be a unitary structure or can be formed as two separate structures that are permanently or detachably coupled together.

Figure 3A:
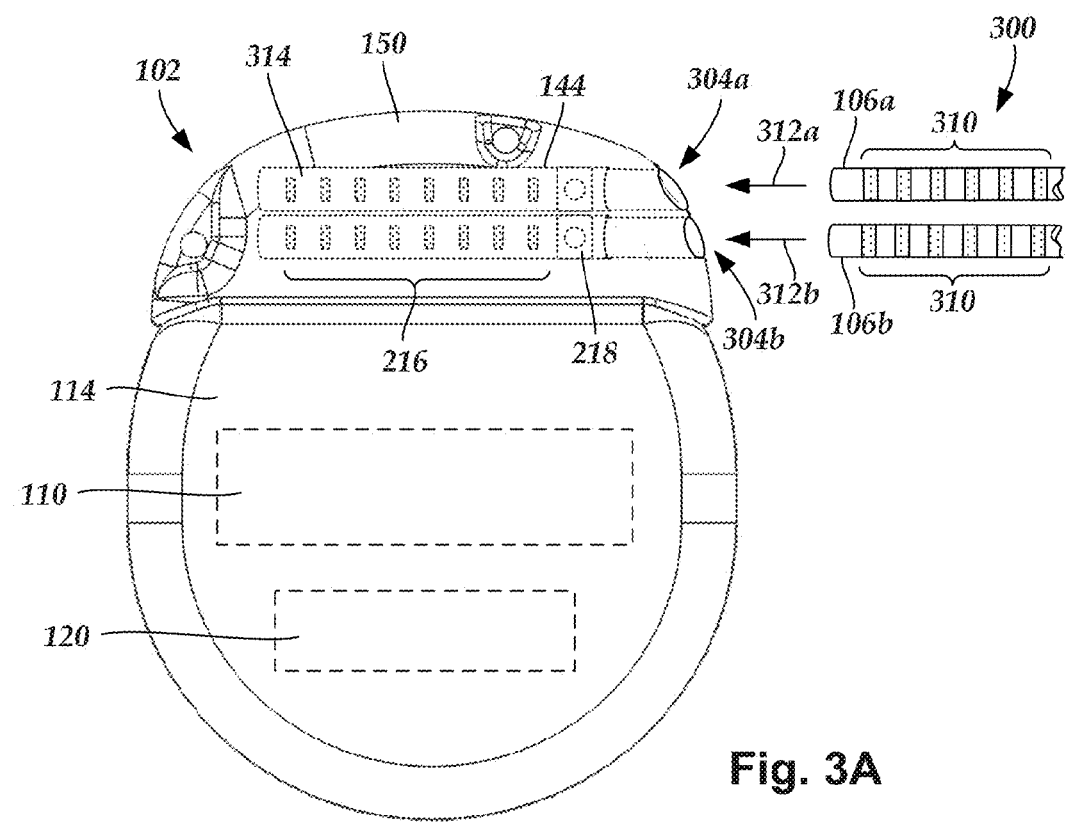
FIG. 3A is a schematic view of one embodiment of the control module of FIG. 1 configured and arranged to electrically couple to an elongated device, according to the invention.
Figure 3B:
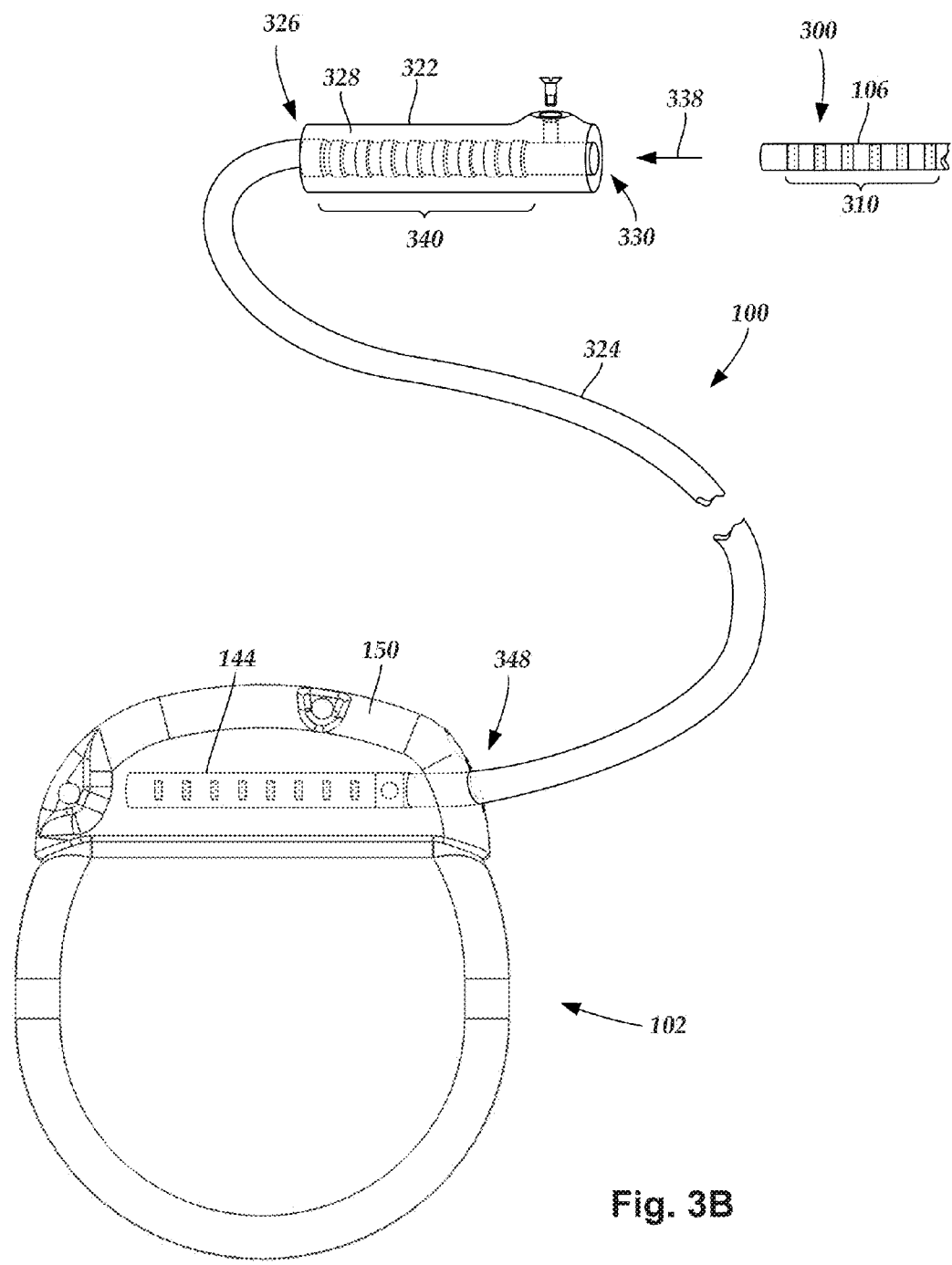
FIG. 3B is a schematic view of one embodiment of a lead extension configured and arranged to electrically couple the elongated device of FIG. 2 to the control module of FIG. 1, according to the invention.

Terminals (e.g., 310 in FIGS. 3A-3B) are typically disposed along the proximal end of the one or more lead bodies 106 of the electrical stimulation system 100 (as well as any splitters, lead extensions, adaptors, or the like) for electrical connection to corresponding connector contacts (e.g., 314 in FIGS. 3A-3B). The connector contacts are disposed in connectors (e.g., 144 in FIGS. 1-3B; and 322 FIG. 3B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 3A is a schematic side view of one embodiment of a proximal end of one or more elongated devices 300 configured and arranged for coupling to one embodiment of the control module connector 144. The one or more elongated devices may include, for example, one or more of the lead bodies 106 of FIG. 1, one or more intermediate devices (e.g., a splitter, the lead extension 324 of FIG. 3B, an adaptor, or the like or combinations thereof), or a combination thereof.

The control module connector 144 defines at least one port into which a proximal end of the elongated device 300 can be inserted, as shown by directional arrows 312a and 312b. In FIG. 3A (and in other figures), the connector housing 112 is shown having two ports 304a and 304b. The connector housing 112 can define any suitable number of ports including, for example, one, two, three, four, five, six, seven, eight, or more ports.

The control module connector 144 also includes a plurality of connector contacts, such as connector contact 314, disposed within each port 304a and 304b. When the elongated device 300 is inserted into the ports 304a and 304b, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

FIG. 3B is a schematic side view of another embodiment of the electrical stimulation system 100. The electrical stimulation system 100 includes a lead extension 324 that is configured and arranged to couple one or more elongated devices 300 (e.g., one of the lead bodies 106 of FIGS. 1 and 2, the splitter 207 of FIG. 2, an adaptor, another lead extension, or the like or combinations thereof) to the control module 102. In FIG. 3B, the lead extension 324 is shown coupled to a single port 304 defined in the control module connector 144. Additionally, the lead extension 324 is shown configured and arranged to couple to a single elongated device 300. In alternate embodiments, the lead extension 324 is configured and arranged to couple to multiple ports 304 defined in the control module connector 144, or to receive multiple elongated devices 300, or both.

A lead extension connector 322 is disposed on the lead extension 324. In FIG. 3B, the lead extension connector 322 is shown disposed at a distal end 326 of the lead extension 324. The lead extension connector 322 includes a connector housing 328. The connector housing 328 defines at least one port 330 into which terminals 310 of the elongated device 300 can be inserted, as shown by directional arrow 338. The connector housing 328 also includes a plurality of connector contacts, such as connector contact 340. When the elongated device 300 is inserted into the port 330, the connector contacts 240 disposed in the connector housing 328 can be aligned with the terminals 310 of the elongated device 300 to electrically couple the lead extension 324 to the electrodes (134 of FIGS. 1 and 2) disposed along the lead (103 in of FIGS. 1 and 2).

In at least some embodiments, the proximal end of the lead extension 324 is similarly configured and arranged as a proximal end of the lead 103 (or other elongated device 300). The lead extension 324 may include a plurality of electrically conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed along the proximal end 348 of the lead extension 324. In at least some embodiments, the proximal end 348 of the lead extension 324 is configured and arranged for insertion into a connector disposed in another lead extension (or another intermediate device). In other embodiments (and as shown in of FIG. 3B), the proximal end 348 of the lead extension 324 is configured and arranged for insertion into the control module connector 144.

A lead can be anchored in patient tissue using a lead anchor. The lead is positioned and held within the lead anchor and then the lead anchor is attached to patient tissue.

Figure 4A:
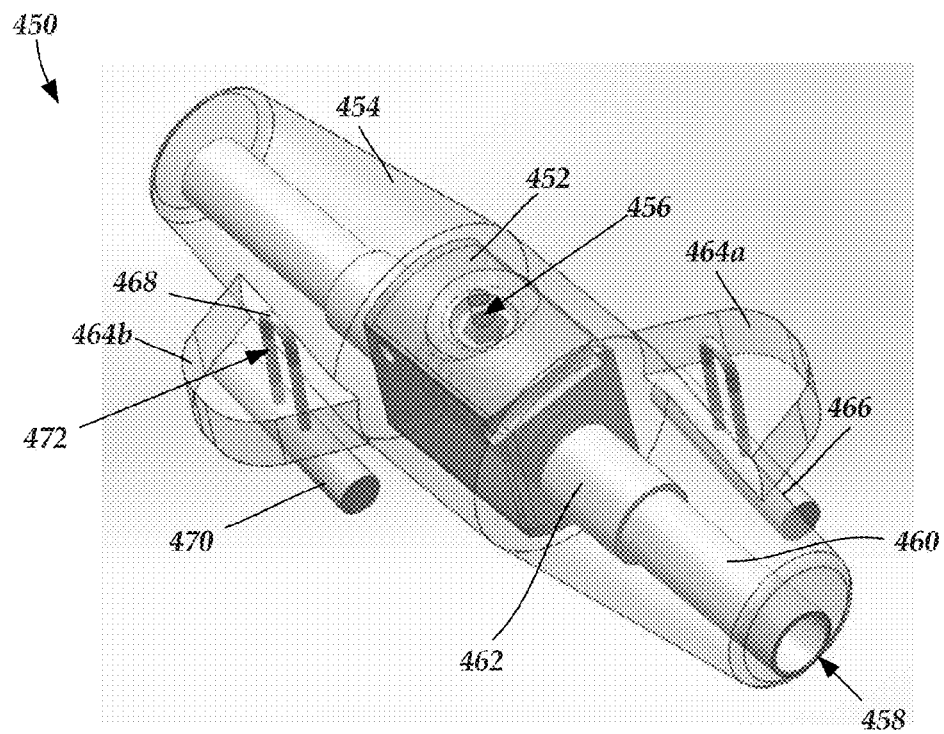
FIG. 4A is schematic perspective top view of one embodiment of a lead anchor, according to the invention.

FIG. 4A is a schematic perspective top view of one embodiment of a lead anchor 450. As shown, the lead anchor 450 includes a body 452 (or anchor body 452) having a first end and a second end opposite to the first end. The body 452 of the lead anchor 450 may be formed using any suitable non-conductive, biocompatible material(s) such as, but not limited to, silicone, polyurethane, polyetheretherketone ("PEEK"), nickel, stainless steel, aluminum, titanium, platinum, and the like or combinations thereof. The anchor body 452 defines a longitudinal lead lumen 458, which can extend from the first end of the anchor body 452 to the second end of the anchor body 452, to receive a lead. The lead lumen 458 can be an elongated tubular passageway within the anchor body 452. The lead lumen 458 may have various suitable cross-sectional shapes, such as, but not limited to, rectangular, elliptical, circular, square, triangular, and so forth depending on shape, size and cross-section of the lead.

The lead anchor 450 includes an exterior member 454 disposed around at least a portion of the anchor body 452. The exterior member 454 may further define a groove opening, bore, or any other suitable structure for fixing the lead anchor 450 to or within the tissue. The exterior member 454 can be formed using any suitable biocompatible flexible material(s) such as, but not limited to, a polyvinyl chloride, polyurethane, thermoplastic polyesters, polycarbonate fluoropolymers, and so forth.

In some embodiments, a lead tube 460 defines or includes the lead lumen 458. The lead tube 460 may extend from a distal end of the exterior member 454 to a proximal end of the exterior member 454. The lead tube 460 can receive a portion of the lead. Further, the lead tube 460 may be a tubular structure or have any suitable cross-section(s) according to shape/size/cross-section of the lead or lead lumen 458. The lead tube 460 may include rides, threads, and so forth, for increasing friction or resistance between the lead and the lead tube 460 so as to enable engagement of the lead within the lead tube 460. In one embodiment, the lead tube 460 and the lead may be formed of the same or similar material, such as silicone, to facilitate or ensure connection between the lead and the lead tube 460 because of the sealing property of the material. Further, the lead tube can be formed using any suitable biocompatible material(s) such as, but not limited to, polymers, metals, alloys, plastics, and so forth. More specific examples of the suitable material(s) can include, but are not limited to, titanium, polyurethane, PVC, polycarbonates, aluminum, silicone, and so forth.

The lead anchor 450 also includes a number of tabs, such as, a first tab 464a and a second tab 464b, extending from the anchor body 452 in two directions. For example, a first tab 464a can extend from the anchor body 452 in a first direction and a second tab 464b can extend from the anchor body 452 in a second direction, which may be opposite from the first direction. In some embodiments, the first tab 464a may be located at a first end of the anchor body 452 and the second tab 464b may be located at the second end of the anchor body 452. In alternative embodiments, the first tab 464a and the second tab 464b may be located proximate to a center portion of the anchor body 452. Further, the first tab 464a and the second tab 464b may be located at same end of the anchor body 452, for example, both tabs 464a-464b may be located either at the first end or at the second end. Each of the first and second tabs 464a-464b includes an eyelet through which a suture can pass through. In some embodiments, when the exterior member 454 is disposed over the anchor body 452, either the tabs 464a-464b may form a unitary structure with the exterior member 454 or may be formed separately and disposed over or on the exterior member 454. The tabs 464a-464b may be attached to the exterior member 454 through any suitable means, such as, but not limited to, adhesive bonding, heat bonding, pressure bonding, and so forth.

Figure 4B:
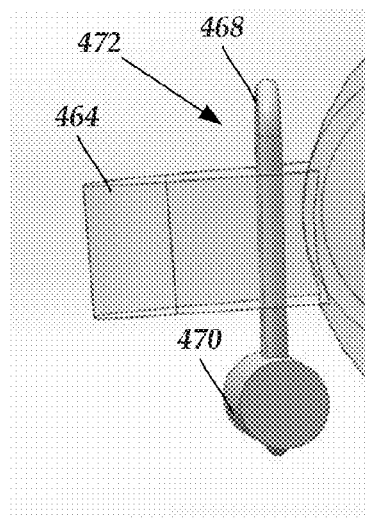
FIG. 4B is a schematic perspective close-up view of a portion of the lead anchor of FIG. 4A.

FIG. 4B is a schematic perspective close-up view of a portion of the lead anchor 450 of FIG. 4A. As shown, the lead anchor 450 also includes a number of anchoring tags 466. Though only two anchoring tags are shown, but there can be any number of tags 466 depending on the number of tabs 464 and/or size/shape/structure of the lead anchor 450. In some embodiments, a first tag 466 is affixed to the first tab 464a and a second tag 466 is affixed to the second tab 464b. Each of the tabs 464a-464b can be molded around respective anchoring tag 466, thereby fixing the anchoring tags 466 with the tabs 464a-464b. Further, the anchoring tags 466 can be routed through the tabs 464a-464b of the lead anchor 450.

Each of the anchoring tags 466 includes an anchor attachment element 468 and a cylindrical implantation element 470. Further, the anchor attachment element 468 may be metallic or plastic or any other suitable biocompatible polymer or synthetic material. Each anchor attachment element 468 defines a suture opening 472 through which a suture can pass. The cylindrical implantation element 470 may be formed using any suitable metal, alloy or biocompatible polymer, such as, but not limited to, titanium, steel, silicone, PVC, polyurethane, and so forth. In some embodiments, there may be some adjustments to the location of the anchoring tag 466, for example, each tag 466 may be located at an angle to better accommodate loading of the tags 466 (or lead anchor 450) into a needle insertion tool 476. The anchor attachment element 468 may have any suitable shape, such as, but not limited to, circular, rectangular, U shape, and so forth.

Figure 4C:
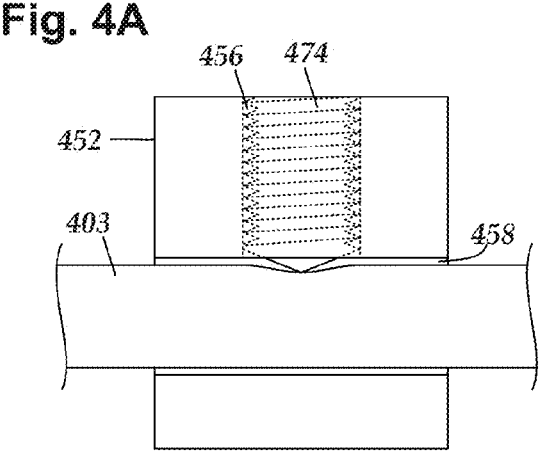
FIG. 4C is schematic cross-sectional view of the anchor body of FIG. 4A, according to the invention.

FIG. 4C is a schematic cross-sectional view of the anchor body 452 of FIG. 4A. The anchor body 452 defines a transverse lumen 456 extending from the top end of the anchor body 452 and perpendicularly intersecting the lead lumen 458. The transverse lumen 456 may have any suitable cross-section, such as, but not limited to, circular, triangular, rectangular, elliptical, and so forth. In some embodiments, the transverse lumen 456 may be in the form of a cylindrical bore in the anchor body 452.

The lead anchor 450 includes a fastening mechanism, such as a fastener 474, disposed in the transverse lumen 456 of the anchor body 452. The fastener 474 is actuable by a user to fasten a lead within the lead anchor 450 by engaging the lead either directly or indirectly (e.g., by engaging a sleeve or part of the lumen tube between the fastener and the lead). The transverse lumen 456 may also include one or more of thread(s), rib(s), groove(s), channel(s), and so forth, to engage the fastener 474 within.

Turning again to FIG. 4A, the lead anchor 450 may also include a sleeve 462 disposed within the lead lumen 458. The sleeve 462 may extend from a first end of the exterior member 454 to a second end of the exterior member 454 or may be extend a shorter length. The sleeve 462 can dissipate force transferred from the fastener 474 to the lead, to thereby reduce, mitigate or prevent damage to the lead caused by engagement of the fastener 474. The sleeve 462 may be a substantially tubular body. The sleeve 462 may be formed using any suitable biocompatible polymer, such as, but not limited to, silicone, PVC, polyurethane, and so forth. Further, the sleeve 462 may remain disposed partially or completely over at least a portion of the lead tube 460. In an embodiment, the sleeve 462 is a Pellethane™ sleeve.

Figure 4D:
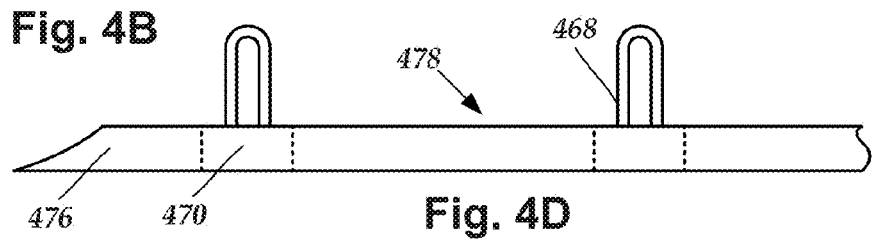
FIG. 4D is a schematic side view of one embodiment of a needle insertion tool for inserting the cylindrical implantation elements of the lead anchor of FIG. 4A.

FIG. 4D is a schematic side view of one embodiment of a needle insertion tool 476 for inserting the cylindrical implantation elements 470 of the lead anchor 450 of FIG. 4A. The needle insertion tool 476 can have a pointed tip portion located at an end of a hollow tubular structure or cannula. The pointed tip portion allows easy insertion of the needle insertion tool 476 into the patient's tissue. The needle insertion tool 476 includes a longitudinal slit 478 extending from a distal end of the needle insertion tool 476 so that the anchoring attachment element(s) can extend out of the needle insertion tool when the anchoring tags 466 are loaded into the tool. The cylindrical implantation element(s) 470 are inserted into the needle insertion tool 476 for implanting into the patient's tissue. The cylindrical implantation element(s) 470 of the anchoring tag(s) 466 can anchor the lead anchor 450 into a patient tissue by insertion of the cylindrical implantation element(s) 470 into the patient tissue using a needle insertion tool 476.

For implantation of the lead 403 and the lead anchor 450 within the patient's body, the lead is loaded into the lead anchor 450 by inserting a portion of the electrical stimulation lead into the lead anchor 450 and fastening the lead anchor 450 to the portion of the lead using a fastening mechanism, such as the fastener 474. The cylindrical implantation elements 470 of the anchoring tags 466 are inserted into the needle insertion tool 476. The needle insertion tool 476 is advanced into a desired anchoring location within the patient's tissue. Then, the first tag 466 (or cylindrical implantation element 470 on the first tag 466) is released by actuating the needle insertion tool 476, such as by pressing a button located at a proximal end of the needle insertion tool 476, into the tissue. Thereafter, the needle insertion tool 476 is directed to another desired anchoring location. Then, the second tag 466 (or cylindrical implantation element 470 on the second tag 466) is released into the tissue by actuating the needle insertion tool 476. The lead anchor can also be sutured to the tissue. For example, a suture folded over the needle insertion tool 476 may form a slip knot and the suture may be tied between the first and the second tags 466. The lead anchor 450 may be sutured to the patient's tissue using a suture that passes through the suture opening 472 of the anchor attachment element 468 of at least one of the anchoring tags 466 by pulling the slip knot.

Figure 5A:
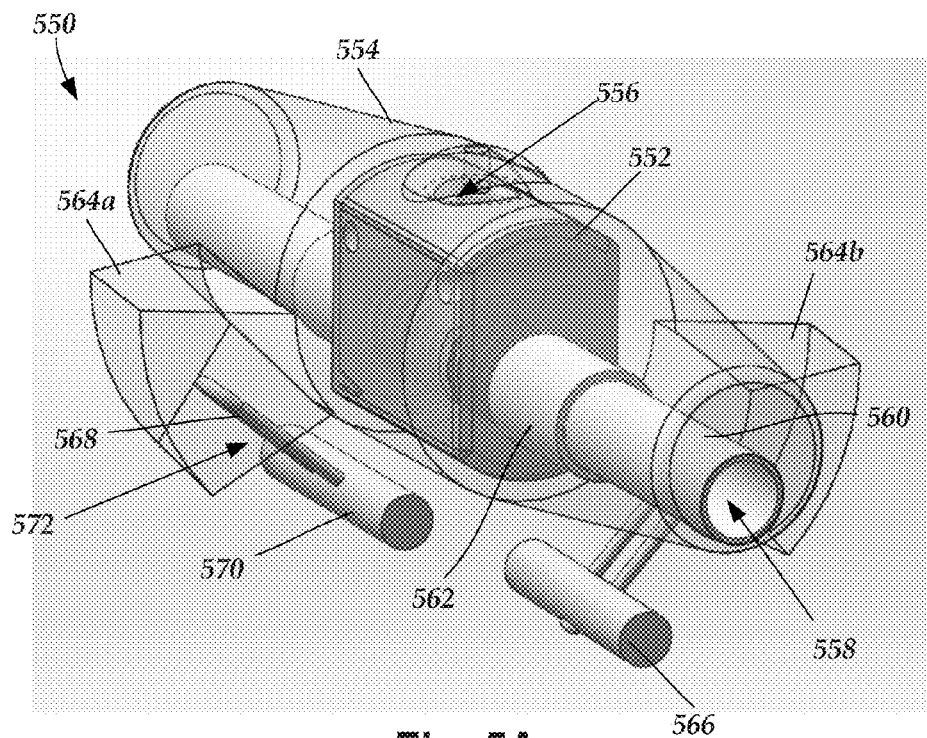
FIG. 5A is schematic perspective side view of a second embodiment of a lead anchor, according to the invention.
Figure 5B:
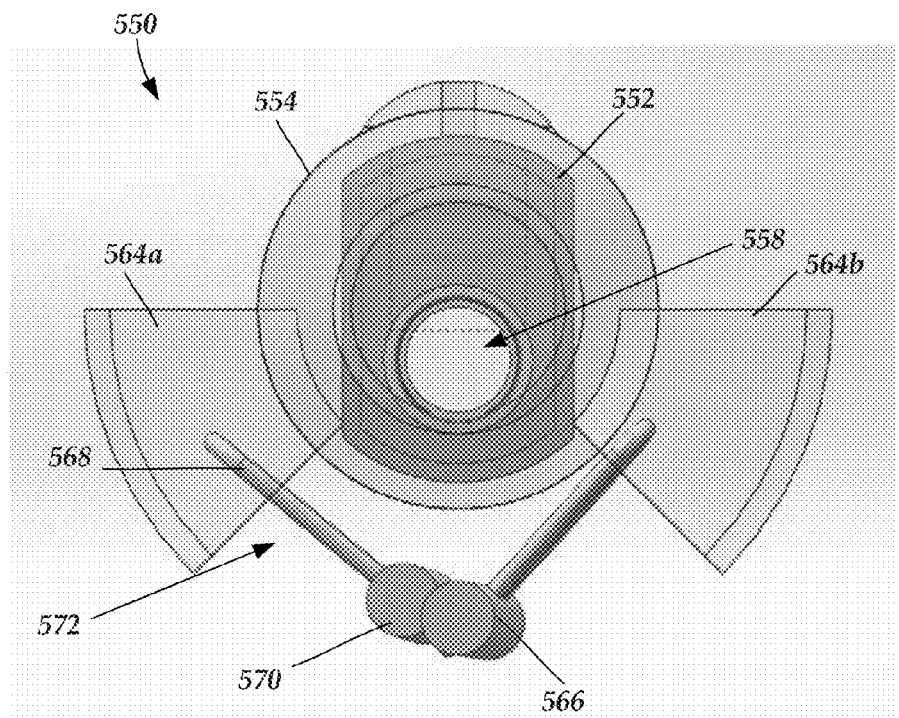
FIG. 5B is schematic front view of the lead anchor of FIG. 5A, according to the invention.

FIG. 5A is a schematic perspective side view of a second embodiment of a lead anchor 550. The lead anchor 550 includes an anchor body 552, an exterior member 554, a transverse lumen 556, a lead lumen 558, a lead tube 560, a sleeve 562, a number of tabs 564a-564b, one or more anchoring tags 566, one or more anchor attachment elements 568, one or more cylindrical implantation elements 570, all of which can be similar or the same in structure and function as compared to one or more structural elements of the lead anchor 450 of FIGS. 4A-4C. The lead anchor 550 includes a first anchoring tag 566 and a second anchoring tag 566. The cylindrical implantation element(s) 570 of the first anchoring tag 566 and second anchoring tag 566 may be angled to permit sequential insertion using the same needle insertion tool 476. The first and second anchoring tags 566 can be at an angle to better accommodate loading of the the cylindrical implantation elements 470 into the needle insertion tool 476. FIG. 5B shows a front view of the lead anchor 550 having angled anchoring tags 566. Further embodiments are now discussed in FIGS. 6A-6B.

Figure 6A:
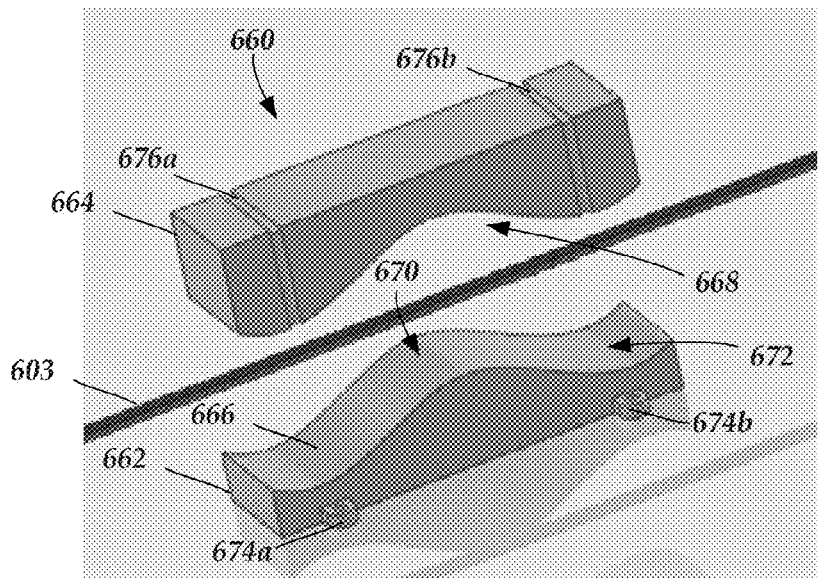
FIG. 6A is schematic perspective side view of a third embodiment of a lead anchor in an open position, according to the invention.

Another type of lead anchor uses a tortuous path to hold the lead within the anchor. FIG. 6A is a schematic perspective side view of such a lead anchor 660 in an open position. The lead anchor 660 includes a first body 662 and a second body 664. The first body 662 includes a top surface 666, a first end, and a second end opposite to the first end. The first body 662 can be formed using any suitable biocompatible materials including PVC (polyvinyl chloride), polyurethane, thermoplastic polyesters, polycarbonate fluoropolymers, gold, silver, titanium, and so forth. The top surface 666 is a wavy or non-flat surface with at least one peak 670, one or more troughs 672, or any combination thereof. In some embodiments, one of the troughs 672 may be defined adjacent to the first end and another of the troughs 672 may be defined adjacent to the second end of the first body 662. The troughs 672 are separated by the peak 670. In some embodiments, the top surface 666 may include more than one peak 670 arranged in an alternating series with respect to the troughs 672. The surface of the peak 670 and the troughs 672 can be smooth and arcuate in order to avoid accidental damage to the lead.

The top surface 666 of the first body receives a portion of a lead extending from the first end to the second end. A lead groove may be formed on the top surface 666, such that the lead can be disposed within the lead groove. The lead groove can be defined as a channel, a cut-out, or a depression in the top surface 666.

The first body 662 also optionally includes suture tabs 674a-674b extending from first body 662 proximate to either one or both of the first and the second ends of the first body 662. The suture tabs 674a-674b may include a suture opening through which a suture can pass. The suture may be passed through the opening of the suture tabs 674a and 674b while fixing the lead anchor 660 into the patient tissue. The suture may be tied around the suture tabs 674a and/or 674b by passing the suture through the opening.

The second body 664 of the lead anchor 660 includes a bottom surface 668, a first end, and a second end opposite to the first end. The bottom surface 668 of the second body 664 conforms to the top surface 666 of the first body 662 so that the first body 662 and second body 664 can be bound together to hold the lead between the first body 662 and the second body 664. The first body 662 and the second body 664 may be formed either from the same or different material. The bottom surface 668 may also include a lead groove in which, at least a portion of the lead can be disposed. The lead groove may be formed using any suitable technique such as, but not limited to, machining, molding or the like.

The second body 664 may further include one or more suture grooves 676a-676b defined over an exterior surface of the second body 664. In one embodiment, the first body 662 may also include suture grooves. The suture grooves 676a-676b may be defined perpendicular to the lead. The two suture grooves 676a-676b can accommodate use of more than one suture. The suture grooves 676a-676b can be considered as any channel or furrow formed over the exterior surface of the second body 664. The suture grooves 676a-676b may be formed using a technique similar to that used to create the lead groove such as machining, molding and so forth. In some embodiments, both the first body 662 and the second body 664 include the suture grooves 676a-676b such that the suture may be disposed in the suture grooves 676a-676b substantially surrounding the lead anchor 660.

In some embodiments, the second body 664 may also include one or more suture tabs extending from an exterior surface of the second body 664 similar to the suture tabs 674a-674b of the first body 662. In at least some embodiments, the anchoring tags 466, as shown in FIG. 4A, can be utilized in conjunction with the suture tabs, as describe above with respect to FIGS. 4A-4D.

As shown, the first body 662 and the second body 664 may be free from each other and may not be in contact when in an open position. In alternative embodiments, the first body 662 and the second body 664 may be connected via a hinge or other connecting mechanism. The hinge or other connecting mechanism couples the first body 662 to the second body 664.

Figure 6B:
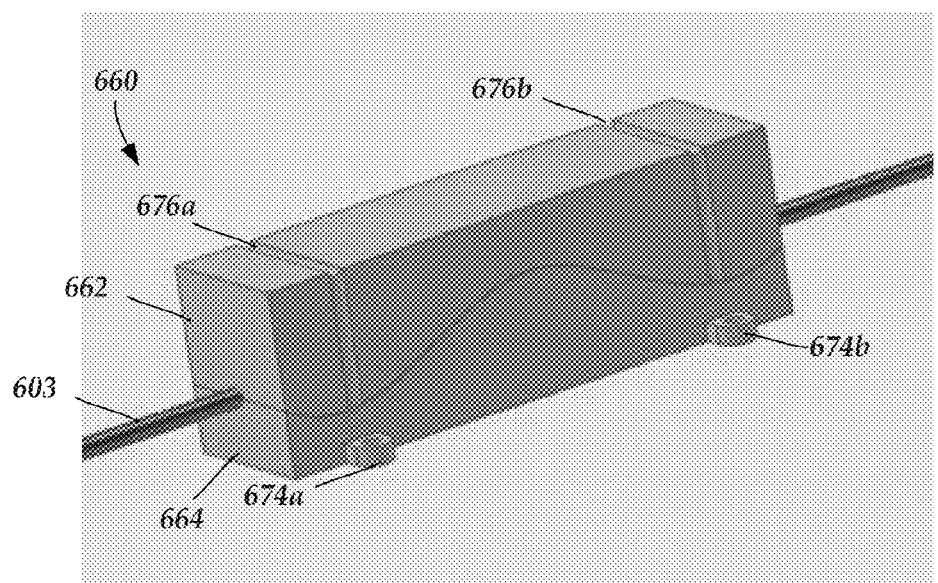
FIG. 6B is schematic perspective side view of the lead anchor of FIG. 6A in the closed position, according to the invention.

FIG. 6B shows the lead anchor 660 in a closed position. A suture may keep the first body 662 engaged or in contact with the second body 664 in the closed position. Once the lead 603 is positioned between the first body 662 and the second body 664, the first body 662, and the second body 664 can be brought together. The second body 664 can sit over the first body 662 for holding the lead within the lead anchor 660. The lead 603 follows a non-linear (e.g., tortuous) path due to the peaks/troughs when placed between the first and second bodies 662 and 664 of the lead anchor. The non-linear path of the lead 603 results in a holding force for engaging the lead 603 securely within the lead anchor 660.

After disposing the lead 603 within the lead anchor 660 and closing the lead anchor 660, a suture may be disposed within and around the suture grooves 676*a*-676*b*. Thereafter, the suture may be passed through the opening in the suture tabs 674*a*-674*b*.

The lead anchor 660 places the lead body in a tortuous path to reduce the likelihood of lead migration. When the lead 603 passes through the lead anchor 660, the peak(s) 670 and the trough(s) 672 hold the lead 603. According to the capstan effect, the interaction of the peak(s) 670 and the trough(s) 672 with the lead 603 may be proportional to the tension caused by bringing together the first body 662 and the second body 664 of the lead anchor 660. The increased tension ensures that the lead anchor 660 hold the lead 603 firmly, thereby avoiding instances of lead migration. The capstan effect allows for higher axial holding force with the same suture tie-down force.

The lead anchor 660 is reversible and the lead anchor 660 can be removed after cutting the suture(s). The lead anchor 660 may have a symmetrical design for facilitating implant within the patient's body.

Another type of lead anchor is an elastic suture ring that can be placed around the lead and then sutured to tissue. FIGS. 7A-7C are schematic side, top, and perspective views, respectively, of one embodiment of an elastic suture ring 770. As shown in FIG. 7A, the elastic suture ring 770 is a substantially circular band. As shown in FIG. 7B, the elastic suture ring 770 includes an opening 776 for the lead. The opening 776 for the lead can be defined by an inner diameter of the elastic suture ring 770.

The elastic suture ring 770 can transit from an expanded state to a collapsed state. In the expanded state, the elastic suture ring 770 is disposed over the portion of the lead such that the lead passes through the opening 776. The elastic suture ring 770 is so disposed over a portion of a lead, such that the elastic suture ring 770 can compressively engage with the portion of the lead. The elastic suture ring 770 may be expanded using, for example, hemostats, a retractor or a suitable spreading tool. When in the expanded state, the inner diameter of the elastic suture ring 770 defines a substantially large opening for lead 776 to be installed in the elastic suture ring 770. Once the elastic suture ring 770 is disposed over the lead, the inner diameter can be allowed to return to a smaller state, such that the inner diameter is smaller than an outer diameter of the lead such that the elastic suture ring 770 is compressively disposed over the lead. In at least some embodiments, the compressive force applied by the elastic suture ring 770 is applied uniformly about 360 degrees and around the lead, such that the compressive force may ensure the engagement of the lead with the elastic suture ring 770. By distributing the force around the lead there is less potential for damage due to stress concentrations and more potential for higher overall axial holding force. The axial holding force for the lead may be dependent on the compressive force of the elastic suture sing 770 on the lead.

The elastic suture ring 770 may possess any suitable cross sectional shape to engage effectively with the lead such as, but not limited to, square, triangular, elliptical, circular, and so forth. The elastic suture ring 770 may be formed from any suitable biocompatible material such as, but not limited to, silicone, silicone rubber, or the like. Further, the elastic suture ring 770 can be formed by using any suitable method such as, but not limited to, stamping, molding, and so forth.

Once the lead is placed securely in the opening 776, the elastic suture ring 770 can be secured within the patient tissue. Any suitable suturing technique may be used with the elastic suture ring 770 to anchor the suture ring 770 to patient tissue. Further, the elastic suture band 770 can include one or more ridges 772 for holding or capturing a suture.

The ridges may be formed with the suture ring. Alternatively, the ridges 772 may be formed separately and disposed over the elastic suture ring 770. The ridges 772 may be attached to the elastic suture ring 770 through any suitable method such as, but not limited to, adhesive bonding, thermal bonding, solvent bonding, and so forth. In some embodiments, the elastic suture ring 770 includes two ridges 772. The ridges 772 are separated by a suture groove 774 defined there between. The suture groove 774 can be a depression on a surface of the elastic suture ring 770. The suture groove 774 can receive the suture, which can be tightened to further ensure the engagement of the lead with the elastic suture ring 770.

Figure 8:
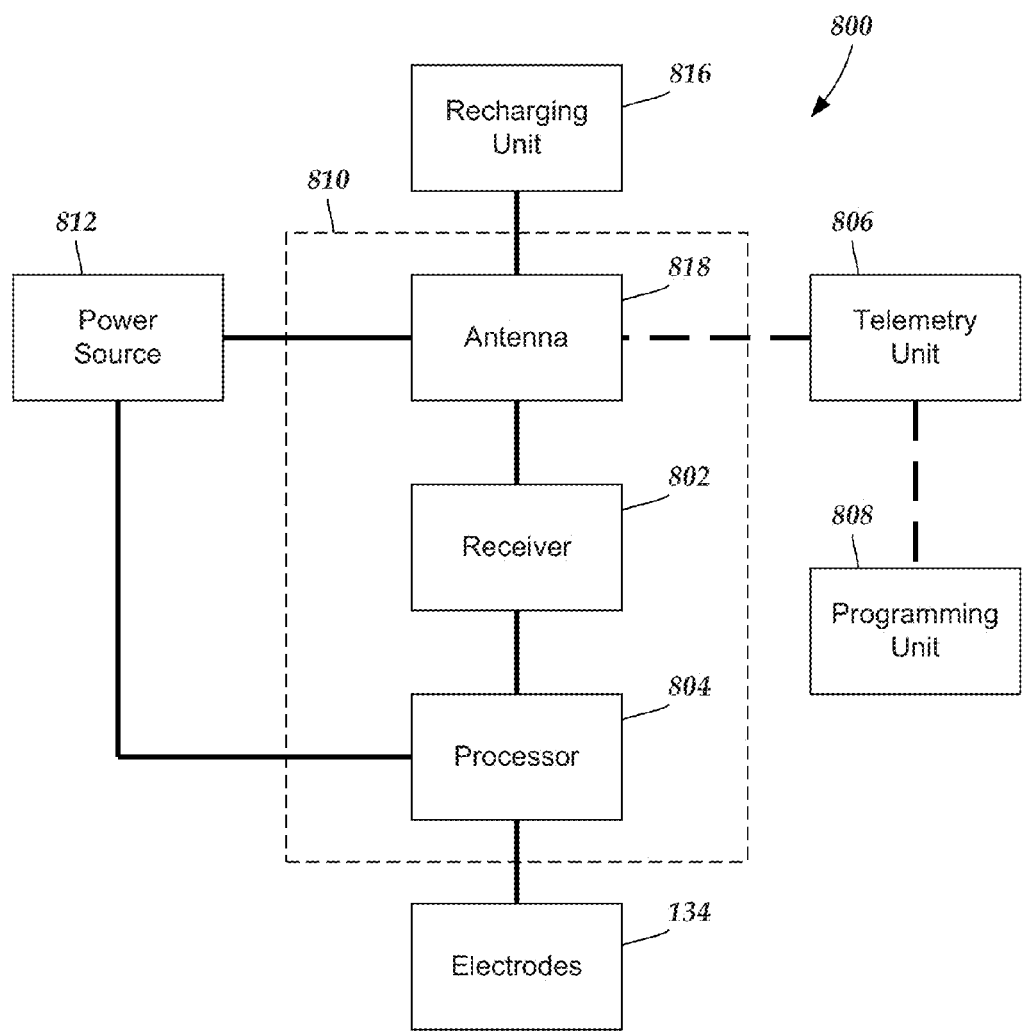
FIG. 8 is a schematic overview of one embodiment of components of a stimulation system, including an electronic subassembly disposed within a control module, according to the invention.

FIG. 8 is a schematic overview of one embodiment of components of an electrical stimulation system 800 including an electronic subassembly 810 disposed within a control module. It will be understood that the electrical stimulation system can include more, fewer, or different components and can have a variety of different configurations including those configurations disclosed in the stimulator references cited herein.

Some of the components (for example, a power source 812, an antenna 818, a receiver 802, and a processor 804) of the electrical stimulation system can be positioned on one or more circuit boards or similar carriers within a sealed housing of an implantable pulse generator, if desired. Any power source 812 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 818 or a secondary antenna. The external power source can be in a device that is mounted on the skin of the user or in a unit that is provided near the user on a permanent or periodic basis.

If the power source 812 is a rechargeable battery, the battery may be recharged using the optional antenna 818, if desired. Power can be provided to the battery for recharging by inductively coupling the battery through the antenna to a recharging unit 816 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 804 is generally included to control the timing and electrical characteristics of the electrical stimulation system. For example, the processor 804 can, if desired, control one or more of the timing, frequency, strength, duration, and waveform of the pulses. In addition, the processor 804 can select which electrodes can be used to provide stimulation, if desired. In some embodiments, the processor 804 selects which electrode(s) are cathodes and which electrode(s) are anodes. In some embodiments, the processor 804 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 808 that, for example, allows modification of pulse characteristics. In the illustrated embodiment, the processor 804 is coupled to a receiver 802 which, in turn, is coupled to the optional antenna 818. This allows the processor 804 to receive instructions from an external source to, for example, direct the pulse characteristics and the selection of electrodes, if desired.

In one embodiment, the antenna 818 is capable of receiving signals (e.g., RF signals) from an external telemetry unit 806 which is programmed by the programming unit 808. The programming unit 808 can be external to, or part of, the telemetry unit 806. The telemetry unit 806 can be a device that is worn on the skin of the user or can be carried by the user and can have a form similar to a pager, cellular phone, or remote control, if desired. As another alternative, the telemetry unit 806 may not be worn or carried by the user but may only be available at a home station or at a clinician's office. The programming unit 808 can be any unit that can provide information to the telemetry unit 806 for transmission to the electrical stimulation system 800. The programming unit 808 can be part of the telemetry unit 806 or can provide signals or information to the telemetry unit 806 via a wireless or wired connection. One example of a suitable programming unit is a computer operated by the user or clinician to send signals to the telemetry unit 806.

The signals sent to the processor 804 via the antenna 818 and the receiver 802 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 800 to cease operation, to start operation, to start charging the battery, or to stop charging the battery. In other embodiments, the stimulation system does not include the antenna 818 or receiver 802 and the processor 804 operates as programmed.

Optionally, the electrical stimulation system 800 may include a transmitter (not shown) coupled to the processor 804 and the antenna 818 for transmitting signals back to the telemetry unit 806 or another unit capable of receiving the signals. For example, the electrical stimulation system 800 may transmit signals indicating whether the electrical stimulation system 800 is operating properly or not or indicating when the battery needs to be charged or the level of charge remaining in the battery. The processor 804 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A lead anchor comprising:
    a body having a first end and a second end opposite to the first end, the body defining a lead lumen extending from the first end to the second end and configured and arranged to receive a lead;
    a fastening mechanism disposed in the body and in communication with the lead lumen and actuable by a user, the fastening mechanism configured and arranged for fastening the received lead to the lead anchor when actuated by the user;
    a plurality of tabs extending from the body; and
    a plurality of anchoring tags, each anchoring tag comprising an anchor attachment element and a cylindrical implantation element coupled to the anchor attachment element, wherein the anchor attachment element is directly fixed to, with a portion molded within, one of the tabs of the lead anchor and the cylindrical implantation element is configured and arranged to anchor the lead anchor into patient tissue by insertion of the implantation element into the patient tissue using a needle insertion tool.

2. The lead anchor of claim 1, wherein the plurality of tabs comprises a first tab extending from the body in a first direction and a second tab extending from the body in a second direction opposite from the first direction and wherein the plurality of anchoring tags comprises a first tag affixed to the first tab and a second tag affixed to the second tab.

3. The lead anchor of claim 2, wherein the cylindrical implantation elements of the first and second tags are angled to permit sequential insertion using a same needle insertion tool.

4. The lead anchor of claim 1, wherein the plurality of tabs comprises a first tab and a second tab extending from the body opposite the first tab.

5. The lead anchor of claim 4, wherein the plurality of anchoring tags comprise a first anchoring tag and a second anchoring tag, wherein a portion of the anchor attachment element of the first anchoring tag extends into and through the first tab and a portion of the anchor attachment element of the second anchoring tag extends into and through the second tab.

6. The lead anchor of claim 1, wherein the anchor attachment element of each anchoring tab is made of metal.

7. The lead anchor of claim 1, wherein the body comprises a transverse lumen in communication with the lead lumen and the fastening mechanism comprises a fastener disposed in the transverse lumen and configured and arranged for engaging the lead directly or indirectly for fastening the lead to the lead anchor.

8. The lead anchor of claim 7, wherein the fastener is a set screw.

9. The lead anchor of claim 1, wherein each anchor attachment element comprises a U-shaped portion extending out of a one of the tabs.

10. The lead anchor of claim 9, wherein each anchor attachment element defines a suture opening through which a suture can pass, wherein the suture opening is disposed between the U-shaped portion and the one of the tabs to which the anchor attachment element is fixed.

11. The lead anchor of claim 1, wherein the lead anchor comprises a same number of tabs and anchoring tags.

12. A method of anchoring a lead, the method comprising:
inserting a portion of an electrical stimulation lead into the lead anchor claim 1;
fastening the lead anchor to the portion of the lead using the fastening mechanism of the lead anchor;
loading one or more of the cylindrical implantation elements into a needle insertion tool;
delivering the one or more the cylindrical implantation elements into patient tissue using the needle insertion tool; and
releasing the one or more of the cylindrical implantation elements within the patient tissue to anchor the lead anchor and lead to the patient tissue.

13. The method of claim 12, wherein each anchor attachment element defines a suture opening through which a suture can pass; and
the method further comprises suturing the lead anchor to the patient tissue using a suture that passes through the suture opening of the anchor attachment element of at least one of the anchoring tags.

14. A kit, comprising:
the lead anchor of claim 1; and
an implantable electrical stimulation lead coupleable to the lead anchor.

15. The kit of claim 14, further comprising a needle insertion tool for implanting the cylindrical implantation elements of the lead anchor.

16. A lead anchor comprising:
a body having a first end and a second end opposite to the first end, the body defining a lead lumen extending from the first end to the second end and configured and arranged to receive a lead;
a fastening mechanism disposed in the body and in communication with the lead lumen and actuable by a user, the fastening mechanism configured and arranged for fastening the received lead to the lead anchor when actuated by the user;
a plurality of tabs extending from the body, wherein one of the tabs includes a first surface and an opposing second surface; and
a plurality of anchoring tags, each anchoring tag comprising an anchor attachment element and a cylindrical implantation element coupled to the anchor attachment element,
wherein the anchor attachment element includes a first portion, an intermediate portion, and a second portion, the first portion extending from the first surface and coupled to the cylindrical implantation element, the intermediate portion is directly fixed to and embedded within one of the tabs, and the second portion extending from the opposing second surface, the second portion defining a suture opening through which a suture can pass, and wherein the cylindrical implantation element is configured and arranged to anchor the lead anchor into patient tissue.

17. The lead anchor of claim 16, wherein the anchor attachment element is rigid.

18. The lead anchor of claim 16, wherein the anchor attachment element includes at least one leg portion embedded within the tab.

19. The lead anchor of claim 16, wherein the at least one leg portion is rigid.

* * * * *